(12) United States Patent
Al-Shammari et al.

(10) Patent No.: US 10,308,733 B2
(45) Date of Patent: Jun. 4, 2019

(54) SYSTEMS AND METHODS RELATED TO THE PRODUCTION OF POLYETHYLENE

(71) Applicant: SABIC Global Technologies B.V., Bergen op Zoom (NL)

(72) Inventors: Talal Al-Shammari, Riyadh (SA); Khalid Karim, Riyadh (SA); Zeeshan Nawaz, Riyadh (SA); Abdullah Turki Al-Jaloud, Riyadh (SA); Shehzada Khurram, Riyadh (SA); Ali Al-Hammad, Riyadh (SA); Mubarik Ali Bashir, Riyadh (SA); Labeeb Chaudhary Ahmed, Riyadh (SA); Saud Al-Khudeer, Riyadh (SA); Thabet Al-Qahtani, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 15/551,415

(22) PCT Filed: Feb. 16, 2016

(86) PCT No.: PCT/IB2016/050825
§ 371 (c)(1),
(2) Date: Aug. 16, 2017

(87) PCT Pub. No.: WO2016/132293
PCT Pub. Date: Aug. 25, 2016

(65) Prior Publication Data
US 2018/0044445 A1    Feb. 15, 2018

Related U.S. Application Data

(60) Provisional application No. 62/118,061, filed on Feb. 19, 2015.

(51) Int. Cl.
*C07C 1/02* (2006.01)
*C07C 1/04* (2006.01)
(Continued)

(52) U.S. Cl.
CPC ............. *C08F 10/02* (2013.01); *C07C 1/02* (2013.01); *C07C 1/04* (2013.01); *C07C 5/32* (2013.01);
(Continued)

(58) Field of Classification Search
None
See application file for complete search history.

(56) References Cited

U.S. PATENT DOCUMENTS 2,506,065 A    5/1950  Alfred
2,850,550 A    9/1958  Reinmuth
(Continued)

FOREIGN PATENT DOCUMENTS

CN    102604677    7/2012
CN    103626898    3/2014
(Continued)

OTHER PUBLICATIONS

CN103626898A, Mar. 12, 2014, pp. 1-12; Machine translation (Year: 2014).*
(Continued)

*Primary Examiner* — Medhanit W Bahta
(74) *Attorney, Agent, or Firm* — Ballard Spahr LLP

(57) ABSTRACT

Disclosed herein is a method comprising the steps of: a) producing a hydrocarbon stream from syngas via a Fischer-Tropsch reaction, wherein the hydrocarbon stream comprises a first C2 hydrocarbon stream comprising ethane and a first ethylene product; b) separating at least a portion of the first C2 hydrocarbon stream from the hydrocarbon stream; c) separating at least a portion of the first ethylene product from
(Continued)

the first C2 hydrocarbon stream, thereby producing a second C2 hydrocarbon stream; d) converting at least a portion of the ethane in the second C2 hydrocarbon stream to a second ethylene product; and e) producing polyethylene from at least a portion of the second ethylene product.

14 Claims, 2 Drawing Sheets

(51) Int. Cl.
    *C07C 5/32*     (2006.01)
    *C07C 9/06*     (2006.01)
    *C07C 11/04*     (2006.01)
    *C08F 2/00*     (2006.01)
    *C08F 10/02*     (2006.01)
    *C10G 2/00*     (2006.01)
    *C10G 50/00*     (2006.01)

(52) U.S. Cl.
    CPC .................. *C08F 2/00* (2013.01); *C10G 2/00* (2013.01); *C10G 2/30* (2013.01); *C10G 2/40* (2013.01); *C10G 50/00* (2013.01); *C10G 2300/1022* (2013.01); *C10G 2400/20* (2013.01)

(56) References Cited

U.S. PATENT DOCUMENTS

| | | | |
|---|---|---|---|
| 3,284,526 | A | 11/1966 | Frayer et al. |
| 3,914,332 | A | 10/1975 | Dickason |
| 4,088,671 | A | 5/1978 | Kobylinski |
| 4,207,248 | A | 6/1980 | Butter et al. |
| 4,463,206 | A | 7/1984 | Derrien et al. |
| 5,306,854 | A | 4/1994 | Choudhary et al. |
| 5,785,739 | A | 7/1998 | Baker |
| 5,791,161 | A | 8/1998 | Manley |
| 5,831,108 | A | 11/1998 | Grubbs et al. |
| 5,968,343 | A | 10/1999 | Drake et al. |
| 5,990,970 | A | 11/1999 | Choi |
| 6,077,985 | A | 6/2000 | Stork |
| 6,291,734 | B1 | 9/2001 | Stork |
| 6,392,109 | B1 | 5/2002 | O'Rear et al. |
| 7,417,173 | B2 | 8/2008 | Crone et al. |
| 7,554,002 | B2 | 6/2009 | Pham Duc |
| 8,066,868 | B1 | 11/2011 | Zimmermann |
| 8,222,472 | B2 | 7/2012 | Chung et al. |
| 8,268,897 | B2 | 9/2012 | Huffman |
| 8,309,616 | B2 | 11/2012 | Huffman |
| 2005/0171311 | A1 | 8/2005 | Schindler et al. |
| 2007/0249793 | A1 | 10/2007 | Vanderbilt |
| 2009/0156870 | A1 | 6/2009 | Lauritzen et al. |
| 2010/0048968 | A1 | 2/2010 | Lauritzen et al. |
| 2010/0069589 | A1 | 3/2010 | Bradin |
| 2011/0207979 | A1 | 8/2011 | Kim et al. |
| 2012/0088944 | A1 | 4/2012 | Buijs et al. |
| 2013/0248419 | A1 | 9/2013 | Abba et al. |
| 2014/0128486 | A1 | 5/2014 | Karim |
| 2014/0200377 | A1 | 7/2014 | Yanagawa et al. |
| 2018/0118639 | A1 | 5/2018 | Al-Qahtani et al. |
| 2018/0134966 | A1 | 5/2018 | Al-Qahtani et al. |

FOREIGN PATENT DOCUMENTS

| | | |
|---|---|---|
| EP | 0082702 A1 | 6/1983 |
| EP | 1035094 | 9/2000 |
| WO | WO-2013/182534 A1 | 12/2013 |
| WO | WO-2016/132293 A1 | 8/2016 |
| WO | WO-2016/185334 A1 | 11/2016 |
| WO | WO-2016/185335 A1 | 11/2016 |

OTHER PUBLICATIONS

Sanfilippo, D. et al. (1992). "Fluidized bed reactors for paraffins dehydrogenation." Chem Eng Sci. 47(9-11): 2313-8.

International Search Report and Written Opinion dated May 17, 2016 by the International Searching Authority for International Application No. PCT/IB2016/050825, which was filed on Feb. 16, 2016 and published as WO 2016/132293 dated Aug. 25, 2016 (Applicant—Sabic Global Technologies B.V.) (8 pages).

Asaftei, I.V. et. al. "Aromatization of industrial feedstock mainly with butanes and butenes over HZSM-5 and Zn/HZSM-5 catalysts", Acta Chennica Lasi, 17 (2009), pp. 5-34. (Year: 2009).

Nijs, H. H.; Jacobs, P. A. "On-Line Single Run Analysis of Effluents from a Fischer-Tropsch Reactor", Journal of Chromatographic Science (1981), 19; pp. 40-45. (Year: 1981).

Park, J.-H. et. al. "Oxidative dehydrogenation of 1-butene to 1,3-butadiene over BiFe0.65NixMo oxide catalysts; Effect of nickel content", Catalysis Communications (2013), 31; pp. 76-80. (Year: 2013).

Sterrett, J. S. et. al. "Kinetics of the Oxidative Dehydrogenation of Butene to Butadiene over a Ferrite Catalyst", Ind. Eng. Chem., 1974), 13; pp. 54-59. (Year: 1974).

Zhang, J. et. al. "Surface-Modified Carbon Nanotubes Catalyze Oxidative Dehydrogenation of n-Butane"; Science (2008), 322; pp. 73-77. (Year: 2008).

International Preliminary Report on Patentability dated Aug. 22, 2017 by the International Searching Authority for International Application No. PCT/IB2016/050825, filed on Feb. 16, 2016 and published as WO/2016/132293 dated Aug. 25, 2016 (Applicant—Sabic Global Technologies B.V.) (5 Pages).

International Search Report and Written Opinion dated Aug. 19, 2016 by the International Searching Authority for International Application No. PCT/IB2016/052752, filed on May 12, 2016 and published as WO 2016/185334 dated Nov. 24, 2016 (Applicant—Sabic Global Technologies B.V.) (11 Pages).

International Preliminary Report on Patentability dated Nov. 21, 2017 by the International Searching Authority for International Application No. PCT/IB2016/052752, filed on May 12, 2016 and published as WO 2016/185334 dated Nov. 24, 2016 (Applicant—Sabic Global Technologies B.V.) (8 Pages).

International Search Report and Written Opinion dated Aug. 19, 2016 by the International Searching Authority for International Application No. PCT/IB2016/052753, filed on May 12, 2016 and published as WO 2016/185335 dated Nov. 24, 2016 (Applicant—Sabic Global Technologies B.V.) (9 Pages).

International Preliminary Report on Patentability dated Nov. 21, 2017 by the International Searching Authority for International Application No. PCT/IB2016/052753, filed on May 12, 2016 and published as WO 2016/185335 dated Nov. 24, 2016 (Applicant—Sabic Global Technologies B.V.) (7 Pages).

* cited by examiner

SYSTEMS AND METHODS RELATED TO THE PRODUCTION OF POLYETHYLENE

CROSS-REFERENCE TO RELATED APPLICATIONS

This is a U.S. National Phase Application of International Application No. PCT/IB2016/050825, filed Feb. 16, 2016, which claims the benefit of U.S. Provisional Application No. 62/118,061, filed Feb. 19, 2015, which are both incorporated herein by reference in their entirety.

BACKGROUND

Syngas (mixtures of $H_2$ and CO) can be readily produced from either coal or methane (natural gas) by methods well known in the art and widely commercially practiced around the world. A number of well-known industrial processes use syngas for producing various oxygenated organic chemicals.

The Fischer-Tropsch catalytic process for catalytically producing hydrocarbons from syngas was initially discovered and developed in the 1920's, and was used in South Africa for many years to produce gasoline range hydrocarbons as automotive fuels. The catalysts typically comprised iron or cobalt supported on alumina or titania, and promoters, like rhenium, zirconium, manganese, and the like were sometimes used with cobalt catalysts, to improve various aspects of catalytic performance. The products were typically gasoline-range hydrocarbon liquids having six or more carbon atoms, along with heavier hydrocarbon products.

Today lower molecular weight C1-C5 hydrocarbons (paraffins and/or olefins) are desired and can be obtained from syngas gas via Fischer-Tropsch catalytic process. There is a need to convert the paraffins and/or olefins obtained into other useful compound(s).

Accordingly, there remains a long-term market need for new and improved methods for producing useful compound(s) from syngas via intermediate low molecular weight C1-C5 hydrocarbons, such as from C2 hydrocarbons.

Accordingly, a system and a method useful for the production of polyethylene are described herein.

SUMMARY OF THE INVENTION

Disclosed herein is a system comprising: a) a Fischer-Tropsch reactor comprising a first inlet and a first outlet; b) a deethanizer comprising a second inlet and a second outlet; c) an olefin separator comprising a third inlet and a third outlet; d) an ethane cracker comprising a fourth inlet and a fourth outlet or an ethane dehydrogenator comprising a fifth inlet and a fifth outlet; e) an ethylene oxide reactor comprising a sixth inlet and a sixth outlet, wherein the Fischer-Tropsch reactor is in fluid communication with the deethanizer via a first connector, wherein the first connector is connected to the first outlet of the Fischer-Tropsch reactor and to the second inlet of the deethanizer, wherein the deethanizer is in fluid communication with the olefin separator via a second connector, wherein the second connector is connected to the second outlet of the deethanizer and to the third inlet of the olefin separator, wherein the olefin separator is in fluid communication with the ethane cracker or the ethane dehydrogenator via a third connector, wherein the third connector is connected to the third outlet of the olefin separator and to the fourth inlet of the ethane cracker or to the fifth inlet of the ethane dehydrogenator, wherein the ethane cracker or the ethane dehydrogenator is in fluid communication with the polyethylene reactor via a fourth connector, wherein the fourth connector is connected to the fourth outlet of the ethane cracker or to the fifth outlet of the ethane dehydrogenator and to the sixth inlet of the polyethylene reactor.

Also, disclosed herein is a method comprising the steps of: a) producing a hydrocarbon stream from syngas via a Fischer-Tropsch reaction, wherein the hydrocarbon stream comprises a first C2 hydrocarbon stream comprising ethane and a first ethylene product; b) separating at least a portion of the first C2 hydrocarbon stream from the hydrocarbon stream; c) separating at least a portion of the first ethylene product from the first C2 hydrocarbon stream, thereby producing a second C2 hydrocarbon stream; d) converting at least a portion of the ethane in the second C2 hydrocarbon stream to a second ethylene product; and e) producing polyethylene from at least a portion of the second ethylene product.

Also disclosed herein is a method comprising the steps of: a) producing a hydrocarbon stream from syngas via a Fischer-Tropsch reaction, wherein the hydrocarbon stream comprises a first C2 hydrocarbon stream comprising ethane and a first ethylene product; b) separating at least a portion of the first C2 hydrocarbon stream from the hydrocarbon stream; c) separating at least a portion of the first ethylene product from the C2 hydrocarbon stream, thereby producing a second C2 hydrocarbon stream; d) converting at least a portion the ethane in the second C2 hydrocarbon stream to a second ethylene product; e) combining at least a portion of the first ethylene product and at least a portion of the second ethylene product, thereby producing a third ethylene product; and f) producing polyethylene from at least a portion of the third ethylene product.

Additional advantages will be set forth in part in the description which follows, and in part will be obvious from the description, or can be learned by practice of the aspects described below. The advantages described below will be realized and attained by means of the chemical compositions, methods, and combinations thereof particularly pointed out in the appended claims. It is to be understood that both the foregoing general description and the following detailed description are exemplary and explanatory only and are not restrictive.

DESCRIPTION OF THE FIGURES

The accompanying figures, which are incorporated in and constitute a part of this specification, illustrate several aspects, and together with the description, serve to explain the principles of the invention.

Figure 1:
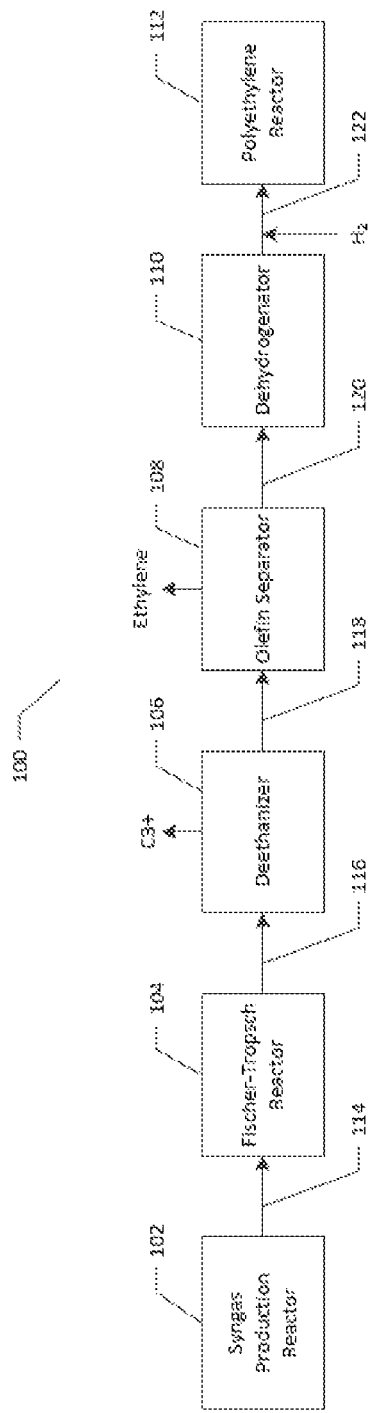
FIG. 1 shows a flow diagram of a method and system disclosed herein.

Additional advantages of the invention will be set forth in part in the description that follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Disclosed herein are materials, compounds, compositions, and components that can be used for, can be used in conjunction with, can be used in preparation for, or are products of the disclosed method and compositions. It is to be understood that when combinations, subsets, interactions, groups, etc. of these materials are disclosed that while specific reference of each various individual and collective combinations and permutation of these compounds cannot be explicitly disclosed, each is specifically contemplated and described herein. This concept applies to all aspects of this disclosure including, but not limited to, steps in methods of making and using the disclosed compositions. Thus, if there are a variety of additional steps that can be performed it is understood that each of these additional steps can be performed with any specific aspect or combination of aspects of the disclosed methods, and that each such combination is specifically contemplated and should be considered disclosed.

1. Definitions

In this specification and in the claims which follow, reference will be made to a number of terms which shall be defined to have the following meanings:

It must be noted that, as used in the specification and the appended claims, the singular forms "a," "an" and "the" include plural referents unless the context clearly dictates otherwise. Thus, for example, reference to "a hydrocarbon" includes mixtures of hydrocarbons.

Ranges can be expressed herein as from one particular value, and/or to " " another particular value. When such a range is expressed, another aspect includes from the one particular value and/or to the other particular value. Similarly, when values are expressed as approximations, by use of the antecedent ",", it will be understood that the particular value forms another aspect. It will be further understood that the endpoints of each of the ranges are significant both in relation to the other endpoint, and independently of the other endpoint.

References in the specification and concluding claims to parts by weight, of a particular element or component in a composition or article, denote the weight relationship between the element or component and any other elements or components in the composition or article for which a part by weight is expressed. Thus, in a compound containing 2 parts by weight of component X and 5 parts by weight of component Y, X and Y are present at a weight ratio of 2:5, and are present in such a ratio regardless of whether additional components are contained in the compound.

A weight percent of a component, unless specifically stated to the contrary, is based on the total weight of the formulation or composition in which the component is included.

2. Fischer-Tropsch Catalytic Process

The Fischer-Tropsch catalytic process for producing hydrocarbons from syngas is known in the art. Several reactions can take place in a Fischer-Tropsch process, such as, a Fischer-Tropsch (FT) reaction, a water gas shift reaction, and a hydrogen methanation, as shown in Scheme 1.

Scheme 1

$n\ CO + 2n\ H_2 \rightarrow (CH_2)_n + H_2O$   FT reaction:

$CO + H_2O \rightarrow CO_2 + H_2$   Water Gas Shift Reaction (WGS):

$CO + H_2 \rightarrow CH_4 + H_2O$   Methanation

The gases that are being mixed in the Fischer-Tropsch process described herein comprise $H_2$ and CO. The $H_2$/CO molar ratio of the feed gas to the first mixing zone can be from 0.5 to 4. For example, the $H_2$/CO molar ratio can be from 1.0 to 3.0, such as, for example, from 1.5 to 3.0, or in another example, from 1.5 to 2.5. It will be appreciated that the $H_2$/CO molar ratio can control the selectivity of the hydrocarbons that are being produced. The consumption molar ratio of $H_2$/CO is usually from about 1.0 to about 2.5, such as for example, from about 1.5 to 2.1, this ratio increases as long as the water gas shift reaction is active and, thus, the use of a feed ratio below the consumption ratio will result in a stable $H_2$/CO ratio during the reaction within an acceptable range (normally below 2). The $H_2$ and CO are catalytically reacted in a Fischer-Tropsch reaction.

A Fischer-Tropsch process that targets the production of light olefins (C2-C10 olefins) is desired and such process can produce a significant amount of a C2 hydrocarbon stream comprising ethane and ethylene. As disclosed herein, a hydrocarbon stream comprising C2 hydrocarbons can undergo processing to be converted into polyethylene.

Polyethylene has the general chemical formula $-(C_2H_4)_n-$. Polyethylene is classified into several different categories based mostly on its density and branching. Its mechanical properties depend significantly on variables such as the extent and type of branching, the crystal structure and the molecular weight. Non-limiting examples polyethylene grades are high-density-polyethylene, low-density-polyethylene, medium-density-polyethylene, ultra-high-molecular-weight-polyethylene, and cross-linked-polyethylene. It is known in the art how to produce the different kind of grades of polyethylene. The system and method disclosed herein are capable of producing polyethylene from a hydrocarbon stream produced in a Fischer-Tropsch Process.

3. System

Disclosed herein is a system comprising: a) a Fischer-Tropsch reactor comprising a first inlet and a first outlet; b) a deethanizer comprising a second inlet and a second outlet; c) an olefin separator comprising a third inlet and a third outlet; d) an ethane cracker comprising a fourth inlet and a fourth outlet or an ethane dehydrogenator comprising a fifth inlet and a fifth outlet; e) an ethylene oxide reactor comprising a sixth inlet and a sixth outlet, wherein the Fischer-Tropsch reactor is in fluid communication with the deethanizer via a first connector, wherein the first connector is connected to the first outlet of the Fischer-Tropsch reactor and to the second inlet of the deethanizer, wherein the deethanizer is in fluid communication with the olefin separator via a second connector, wherein the second connector is connected to the second outlet of the deethanizer and to the third inlet of the olefin separator, wherein the olefin separator is in fluid communication with the ethane cracker or the ethane dehydrogenator via a third connector, wherein the third connector is connected to the third outlet of the olefin separator and to the fourth inlet of the ethane cracker or to the fifth inlet of the ethane dehydrogenator, wherein the ethane cracker or the ethane dehydrogenator is in fluid communication with the polyethylene reactor via a fourth connector, wherein the fourth connector is connected to the fourth outlet of the ethane cracker or to the fifth outlet of the ethane dehydrogenator and to the sixth inlet of the polyethylene reactor.

In one aspect, the system comprises an ethane cracker. In one aspect, the system comprises an ethane dehydrogenator.

In one aspect, the system further comprises a syngas production reactor comprising an seventh outlet, wherein the syngas production reactor is in fluid communication with the Fischer-Tropsch reactor via fifth connector, wherein the Fischer-Tropsch reactor further comprises an eighth inlet, wherein the fifth connector is connected to the seventh outlet of the syngas production reactor and to the eighth inlet of the Fischer-Tropsch reactor.

In one aspect, the olefin separator is in fluid communication with the polyethylene reactor via a sixth connector. In one aspect, the seventh connector is connected to an eight outlet of the olefin reactor and a ninth inlet of polyethylene reactor.

Isothermal and/or adiabatic fixed, moving, or fluidized bed reactors can be used as a Fischer-Tropsch reactor, which can carry out the Fischer-Tropsch process selective to the production of olefins. The Fischer-Tropsch reactor is configured to convert syngas to olefins.

The Fischer-Tropsch reactor can comprise one or more Fischer-Tropsch catalysts. Fischer-Tropsch catalysts are known in the art and can, for example, be Fe based catalysts and/or Co based catalysts and/or Ru based catalysts. Such catalysts are described in U.S. Pat. Nos. 4,088,671 and 4,207,248, which are incorporated herein by their entirety, specifically for their disclosure regarding Fischer-Tropsch catalysts.

A deethanizer is known in the art. A deethanizer separates the C2 hydrocarbon stream, disclosed herein, from the hydrocarbon stream disclosed herein. A deethanizer can be a fractionation column, which uses distillation separation technologies for hydrocarbon separation. Dethanizers are, for example, described in U.S. Pat. No. 7,554,002, European Patent 1035094, and U.S. Pat. No. 5,791,161, which are incorporated herein by their entirety, specifically for their disclosure regarding deethanizers.

A dehydrogenation reactor is a vessel that is configured to convert alkanes (i.e. paraffins) to alkenes (i.e. olefins). For example, the dehydrogenation reactor can be a fixed bed tubular or tube bundle reactor. The conversion of alkanes (i.e. paraffins) to alkenes olefins) is often a catalytic process. For example, a dehydrogenation reactor can convert ethane into ethylene. The dehydrogenation reactor can further comprise a dehydrogenation catalyst, such as, for example, a Pd or V based catalyst.

In one aspect, the catalytic process can, for example, be nonoxidative as described in U.S. Pat. No. 7,417,173. The nonoxidative catalytic ethane dehydrogenation can be carried out under heterogeneous catalysis in a fluidized bed, as described in Chem. Eng. Sci. 1992 b, 47 (9-11) 2313. Appropriately, two fluidized beds can be operated in parallel, of which one is generally in the state of regeneration. The working pressure is typically from 1 to 2 bar, the dehydrogenation temperature generally from 550 to 600° C., The heat required for the dehydrogenation is introduced into the reaction system by preheating the dehydrogenation catalyst to the reaction temperature.

In another aspect, the dehydrogenation can be oxidative. Dehydrogenation catalysts such as V based catalysts are, for example, described in U.S. Pat. No. 3,914,332, which is hereby incorporated by reference, specifically for the disclosure regarding oxidative catalysts.

An ethane cracker a reactor that is configured to heat up ethane to thermally break apart ethane to form ethylene. An ethane cracker is known in the art. An ethane cracker can for example be a steam cracker. Ethane crackers and steam crackers are, for example, described in U.S. Pat. Nos. 5,990,370, and 5,785,739, which are incorporated herein by their entirety, specifically for their disclosure regarding ethane crackers and steam crackers.

An olefin separator is a separator that can separate olefins from paraffins and other products. The olefin separator can be a separator that cryogenically can separate olefins from paraffins. For example, the olefin separator can separate ethylene from a C2 hydrocarbon stream. Olefin separators are known in the art and can also include distillation and membrane separation, or a combination thereof.

A polyethylene reactor is a vessel that is configured to carry out to produce polyethylene from ethylene. The polyethylene reactor can be a fluidized bed reactor. For example, polyethylene can be produced from ethylene via a catalytic reaction. The catalytic reaction is typically highly exothermic. A common class of catalysts for the polymerization of ethylene is titanium(III) chloride type catalysts, or so-called Ziegler-Natta type catalysts. Another common catalyst is the Phillips catalyst, prepared by depositing chromium(VI) oxide on a support material, such as silica.

A syngas production reactor can produce syngas from one or more sources. Syngas can be produced from many sources, including natural gas, coal, biomass, or virtually any hydrocarbon feedstock, by reaction with steam or oxygen. For example, partial oxidation (POX) of methane (or hydrocarbons) is a non-catalytic, large-scale process to make syngas and yields syngas with $H_2/CO$ ratio of about 2. In another example, the syngas reactor can convert natural gas into syngas. As such, the syngas production reactor can be an autothermal reforming (ATR) reactor which combines methane and steam reforming and oxidation in one process. The heat needed for reforming is generated inside the reactor by oxididation of the feed gas (natural gas). ATR is also suitable for large-scale production of syngas for gas-to-liquids or large-scale methanol synthesis processes.

Optionally, in various aspects, the disclosed system can be operated or configured on an industrial scale. In one aspect, the reactors described herein can each be an industrial size reactor. For example, the Fischer-Tropsch reactor can be an industrial size reactor. In another example, the deethanizer can be an industrial size reactor. In yet another example, the dehydrogenation reactor can be an industrial size reactor. In yet another example, the olefin separator can be an industrial size reactor. In yet another example, the dehydrogenator can be an industrial size reactor. In yet another example, the ethane cracker can be an industrial size reactor. In yet another example, the polyethylene reactor can be an industrial size reactor. In yet another example, the ethylene glycol reactor can be an industrial size reactor. In yet another example, the syngas production reactor can be an industrial size reactor.

The reactors disclosed herein can have a volume of at least about 1,000 liters, about 2,000 liters, about 5,000 liters, or about 20,000 liters. For example, the reactor can have a volume from about 1,000 liter to about 20,000 liters.

In one aspect, the Fischer-Tropsch reactor can have a volume of at least about 1,000 liters, about 2,000 liters, about 5,000 liters, or about 20,000 liters. For example, Fischer-Tropsch reactor can have a volume from about 1,000 liter to about 20,000 liters.

In one aspect, the deethanizer can have a volume of at least about 1,000 liters, about 2,000 liters, about 5,000 liters, or about 20,000 liters. For example, deethanizer can have a volume from about 1,000 liter to about 20,000 liters.

In one aspect, the olefin separator can have a volume of at least about 1,000 liters, about 2,000 liters, about 5,000 liters, or about 20,000 liters. For example, the olefin separator can have a volume from about 1,000 liter to about 20,000 liters.

In one aspect, the ethane cracker can have a volume of at least about 1,000 liters, about 2,000 liters, about 5,000 liters, or about 20,000 liters. For example, the ethane cracker can have a volume from about 1,000 liter to about 20,000 liters.

In one aspect, the dehydrogenator can have a volume of at least about 1,000 liters, about 2,000 liters, about 5,000 liters, or about 20,000 liters. For example, the dehydrogenator can have a volume from about 1,000 liter to about 20,000 liters.

In one aspect, the polyethylene reactor can have a volume of at least about 1,000 liters, about 2,000 liters, about 5,000 liters, or about 20,000 liters. For example, the polyethylene reactor can have a volume from about 1,000 liter to about 20,000 liters.

In one aspect, the syngas production reactor can have a volume of at least about 1,000 liters, about 2,000 liters, about 5,000 liters, or about 20,000 liters. For example, the syngas production reactor can have a volume from about 1,000 liter to about 20,000 liters.

In one aspect, the system is capable of producing at least about 100 liters, about 500 liters, about 1,000 liters, about 10,000 liters, or from about 100 to about 10,000 liters, such as from about 250 liters to about 1,000 liters of polyethylene per hour.

Now referring to FIG. 1, which shows a non-limiting exemplary aspect of the system and method disclosed herein. FIG. 1 shows a system (100). The system (100) has a syngas production reactor (102). The syngas production reactor (102) is in fluid communication with a Fischer-Tropsch reactor (104). The Fischer-Tropsch reactor (104) is in further fluid communication with a deethanizer (106). The deethanizer (106) is in further fluid communication with an olefin separator (108). The olefin separator (108) is in further fluid communication with a dehydrogenator (110). The dehydrogenation reactor (110) is in further fluid communication with a polyethylene reactor (112). The syngas production reactor (102) is in fluid communication with a Fischer-Tropsch reactor (104) via a fifth connector (114). The Fischer-Tropsch reactor (104) is in further fluid communication with a deethanizer (106) via a first connector (116). The deethanizer (106) is in further fluid communication with an olefin separator (108) via a second connector (118). The olefin separator (108) is in further fluid communication with a dehydrogenator (110) via a third connector (120). The dehydrogenation reactor (110) is in further fluid communication with a polyethylene reactor (112) via a fourth connector (122).

Figure 2:
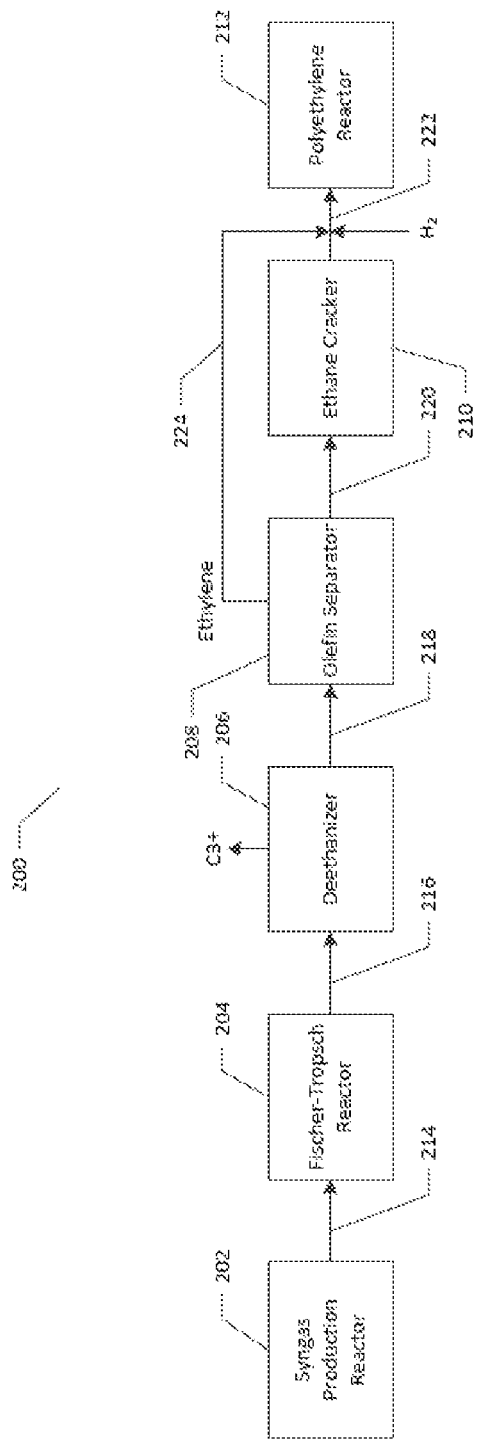
FIG. 2 shows a flow diagram of a method and system disclosed herein.

Now referring to FIG. 2, which shows a non-limiting exemplary aspect of the system and method disclosed herein. FIG. 2 shows a system (200). The system (200) has a syngas production reactor (202). The syngas production reactor (202) is in fluid communication with a Fischer-Tropsch reactor (204). The Fischer-Tropsch reactor (204) is in further fluid communication with a deethanizer (206). The deethanizer (206) is in further fluid communication with an olefin separator (208). The olefin separator (208) is in further fluid communication with an ethane cracker (210). The ethane cracker (210) is in further fluid communication with an polyethylene reactor (212). The syngas production reactor (202) is in fluid communication with a Fischer-Tropsch reactor (204) via a fifth connector (214). The Fischer-Tropsch reactor (204) is in further fluid communication with a deethanizer (206) via a first connector (216). The deethanizer (206) is in further fluid communication with an olefin separator (208) via a second connector (218). The olefin separator (208) is in further fluid communication with an ethane cracker (210) via a third connector (220). The ethane cracker (210) is in further fluid communication with a polyethylene reactor (212) via a fourth connector (222). The olefin separator (208) is in further fluid communication with the polyethylene reactor (212) via a sixth connector (224).

In FIGS. 1 and 2 it is understood that the corresponding components can be identical or the same in both systems. For example, the syngas production reactor (102) in FIG. 1 can be identical or the same as the syngas production reactor (202) in FIG. 2.

4. Methods

Also disclosed herein is a method of producing polyethylene. In one aspect, the method can further produce ethylene glycol. In one aspect, the method can be performed by the system disclosed herein.

Disclosed herein is a method comprising the steps of a) producing a hydrocarbon stream from syngas via a Fischer-Tropsch reaction, wherein the hydrocarbon stream comprises a first C2 hydrocarbon stream comprising ethane and a first ethylene product; b) separating at least a portion of the first C2 hydrocarbon stream from the hydrocarbon stream; c) separating at least a portion of the first ethylene product from the first C2 hydrocarbon stream, thereby producing a second C2 hydrocarbon stream; d) converting at least a portion of the ethane in the second C2 hydrocarbon stream to a second ethylene product; and e) producing polyethylene from at least a portion of the second ethylene product.

Also disclosed herein is a method comprising the steps of: a) producing a hydrocarbon stream from syngas via a Fischer-Tropsch reaction, wherein the hydrocarbon stream comprises a first C2 hydrocarbon stream comprising ethane and a first ethylene product; b) separating at least a portion of the first C2 hydrocarbon stream from the hydrocarbon stream; c) separating at least a portion of the first ethylene product from the C2 hydrocarbon stream, thereby producing a second C2 hydrocarbon stream; d) converting at least a portion the ethane in the second C2 hydrocarbon stream to a second ethylene product; e) combining at least a portion of the first ethylene product and at least a portion of the second ethylene product, thereby producing a third ethylene product; and f) producing polyethylene from at least a portion of the third ethylene product.

In one aspect, the polyethylene is a low-density-polyethylene. Low-density-polyethylene is defined by a density range of 0.910-0.940 g/cm$^3$. Low-density-polyethylene has a high degree of short and long chain branching, which means that the chains do not pack into the crystal structure as well. This results in a lower tensile strength and increased ductility. Low-density-polyethylene is typically made by a free radical polymerization. Low-density-polyethylene is used for both rigid containers and plastic film applications such as, for example, plastic bags and film wrap.

In one aspect, the polyethylene is a medium-density-polyethylene. Medium-density-polyethylene is defined by having a density range of 0.926-0.940 g/cm$^3$. Medium-density-polyethylene can be produced by catalysts such as chromium/silica catalysts, Ziegler-Natta catalysts, or metallocene catalysts. Medium-density-polyethylene has good shock and drop resistance properties. Medium-density-polyethylene is used in many products, such as, but not limited to, gas pipes and fittings, sacks, shrink film, packaging film, and carrier bags.

In one aspect, the polyethylene is a high-density-polyethylene. High-density-polyethylene is defined by having a density of greater or equal to 0.941 g/cm$^3$. High-density-polyethylene has a low degree of branching and thus low intermolecular forces and tensile strength. High-density-polyethylene can be produced by chromium/silica catalysts, Ziegler-Natta catalysts, and metallocene catalysts. The lack of branching, and thus high density, is can be controlled by using an appropriate catalyst and reaction conditions. These are known in the art. High-density-polyethylene is used in many products, such as, but not limited to everyday plastic products, such as, milk jugs, detergent bottles, butter tubs, garbage containers, plastic toys, and water pipes.

In one aspect, the polyethylene is an ultra-high-molecular-weight-polyethylene. Ultra-high-molecular-weight-polyethylene is polyethylene with a molecular weight from about 2,000,000 to about 6,000,000. Ultra-high-molecular-weight polyethylene has typically a density of 0.930-0.935 g/cm$^3$. Ultra-high-molecular-weight polyethylene can be made using standard catalyst technology, such as, for example, Ziegler-Natta type catalysts. Ultra-high-molecular-weight polyethylene is used in a diverse range of applications. These include, but are not limited to, machine parts, moving parts on weaving machines, bearings, gears, artificial joints, edge protection on ice rinks, and cutting boards.

In one aspect, the step of converting at least a portion of the ethane in the second C2 hydrocarbon stream to a second ethylene product comprises dehydrogenating the at least a portion of the ethane in the second C2 hydrocarbon stream.

In one aspect, the step of converting at least a portion the ethane in the second C2 hydrocarbon stream to a second ethylene product comprises cracking the at least a portion of the ethane in the second C2 hydrocarbon stream.

In one aspect, the step of producing polyethylene from at least a portion of the second ethylene product comprises reacting second ethylene product with an oxygenate. For example, the oxygenate can be H$_2$O.

In one aspect, the hydrocarbon stream further comprises C3-C6 hydrocarbons, such as, C3-C6 olefins and paraffins. For example, the hydrocarbon stream can further comprise at least about 30 wt % of C3-C6 olefins and paraffins. In another example, the hydrocarbon stream can further comprise at least about 40 wt % of C3-C6 olefins and paraffins. In yet another example, the hydrocarbon stream can further comprise at least about 50 wt % of C3-C6 olefins and paraffins. In yet another example, the hydrocarbon stream can further comprise at least about 60 wt % of C3-C6 olefins and paraffins. In yet another example, the hydrocarbon stream can further comprise from about 30 wt % to about 70 wt % of C3-C6 olefins and paraffins.

In one aspect, the hydrocarbon stream comprises at least about 5 wt % of a first C2 hydrocarbon stream comprising ethane and a first ethylene product. In one aspect, the hydrocarbon stream comprises at least about 10 wt % of a first C2 hydrocarbon stream comprising ethane and a first ethylene product. In another aspect, the hydrocarbon stream comprises at least about 15 wt % of a first C2 hydrocarbon stream comprising ethane and a first ethylene product. In yet another aspect, the hydrocarbon stream comprises at least about 20 wt % of a first C2 hydrocarbon stream comprising ethane and a first ethylene product. In yet another aspect, the hydrocarbon stream comprises at least about 25 wt % of a first C2 hydrocarbon stream comprising ethane and a first ethylene product. In yet another aspect, the hydrocarbon stream comprises at least about 30 wt % of a first C2 hydrocarbon stream comprising ethane and a first ethylene product.

In one aspect, the hydrocarbon stream comprises from about 5 wt % to about 30 wt % of the first C2 hydrocarbon stream comprising ethane and a first ethylene product. In another aspect, the hydrocarbon stream comprises from about 5 wt % to about 20 wt % of the first C2 hydrocarbon stream comprising ethane and a first ethylene product. In yet another aspect, the hydrocarbon stream stream comprises from about 5 wt % to about 15 wt % of the first C2 hydrocarbon stream comprising ethane and a first ethylene product.

In one aspect, the first C2 hydrocarbon stream comprises at least about 30 wt % of ethane. In another aspect, the first C2 hydrocarbon stream comprises at least about 50 wt % of ethane. In yet another aspect, the first C2 hydrocarbon stream comprises at least about 70 wt % of ethane. For example, the first C2 hydrocarbon stream can comprise at least from about 30 wt % to about 70 wt % of ethane.

In one aspect, the first C2 hydrocarbon stream comprises at least about 30 wt % of ethylene. In another aspect, the first C2 hydrocarbon stream comprises at least about 50 wt % of ethylene. In yet another aspect, the first C2 hydrocarbon stream comprises at least about 70 wt % of ethylene. For example, first C2 hydrocarbon stream can comprise at least from about 30 wt % to about 70 wt % of ethylene.

In one aspect, the first C2 hydrocarbon stream comprises from about 30 wt % to about 70 wt % of ethane and from about 70 wt % to about 30 wt % of the first ethylene product.

The step of separating at least a portion of the first C2 hydrocarbon stream from the hydrocarbon stream can be performed by the deethanizer disclosed herein. In one aspect, at least about 60 wt % of the first C2 hydrocarbon stream in the hydrocarbon stream is separated from the hydrocarbon stream. In another aspect, at least about 80 wt. % of the first C2 hydrocarbon stream in the hydrocarbon stream is separated from the hydrocarbon stream. In yet another aspect, from about 60 wt % to about 95 wt % of the first C2 hydrocarbon stream in the hydrocarbon stream is separated from the hydrocarbon stream.

The step of separating at least a portion of the first ethylene product from the first C2 hydrocarbon stream, thereby producing a second C2 hydrocarbon stream can be performed by the olefin separator disclosed herein. In one aspect, the second C2 hydrocarbon stream comprises at least about 50 wt % of ethane. In another aspect, the second C2 hydrocarbon stream comprises at least about 60 wt % of ethane. In yet another aspect, the second C2 hydrocarbon stream comprises at least about 70 wt % of ethane. In yet another aspect, the second C2 hydrocarbon stream comprises at least about 80 wt % of ethane. In yet another aspect, the second C2 hydrocarbon stream comprises at least about 90 wt % of ethane. In yet another aspect, the second C2 hydrocarbon stream comprises at least from about 50 wt % to about 99 wt % of ethane.

The step of converting at least a portion of the ethane in the second C2 hydrocarbon stream to a second ethylene product can, for example, be performed by the ethane cracker disclosed herein. The step of converting at least a portion of the ethane in the second C2 hydrocarbon stream to a second ethylene product can, in another example, be performed by the ethane dehydrogenator disclosed herein.

In one aspect, the second ethylene product comprises at least about 80 wt % of ethylene. In another aspect, the second ethylene product comprises at least about 85 wt % of ethylene. In yet another aspect, the second ethylene product comprises at least about 90 wt % of ethylene. In yet another aspect, the second ethylene product comprises at least about 95 wt % of ethylene. In yet another aspect, the second ethylene product comprises at least from about 80 wt % to about 99 wt % of ethylene.

The step of producing polyethylene from at least a portion of the second ethylene product can be performed by the polyethylene reactor disclosed herein. In one aspect, at least about 80 wt % of the second ethylene product is converted to polyethylene. In another aspect, at least about 85 wt % of the second ethylene product is converted to polyethylene. In yet another aspect, at least about 90 wt % of the second ethylene product is converted to polyethylene. In yet another aspect, at least about 95 wt. % of second ethylene product is converted to polyethylene. In yet another aspect, at least about from 80 wt % to about 99 wt % of the second ethylene product is converted to polyethylene.

The step of combining at least a portion of the first ethylene product and at least a portion of the second ethylene product, thereby producing a third ethylene product can be performed by the sixth connector from the olefin separator to the polyethylene reactor as disclosed herein.

In one aspect, the third ethylene product comprises at least about 80 wt % of ethylene. In another aspect, the third ethylene product comprises at least about 85 wt % of ethylene. In yet another aspect, the third ethylene product comprises at least about 90 wt % of ethylene. In yet another aspect, the third ethylene product comprises at least about 95 wt % of ethylene. In yet another aspect, the third ethylene product comprises at least from about 80 wt % to about 99 wt % of ethylene.

The step of producing polyethylene from at least a portion of the third ethylene product can be performed by the polyethylene reactor disclosed herein. In one aspect, at least about 80 wt % of the third ethylene product is converted to polyethylene. In another aspect, at least about 85 wt % of the third ethylene product is converted to polyethylene. In yet another aspect, at least about 90 wt % of the third ethylene product is converted to polyethylene. In yet another aspect, at least about 95 wt % of the third ethylene product is converted to polyethylene. In yet another aspect, at least about from 80 wt % to about 99 wt % of the third ethylene product is converted to polyethylene.

In one aspect, the method can produce at least 100 liters of polyethylene per hour. In another aspect, the method can produce at least 500 liters of polyethylene per hour. In yet another aspect, the method can produce at least 1,000 liters of polyethylene per hour. In yet another aspect, the method can produce at least 10,000 liters of polyethylene per hour. For example, the method can produce from 100 to 10,000 liters of polyethylene per hour.

5. Aspects

In view of the described catalyst and catalyst compositions and methods and variations thereof, herein below are described certain more particularly described aspects of the inventions. These particularly recited aspects should not however be interpreted to have any limiting effect on any different claims containing different or more general teachings described herein, or that the "particular" aspects are somehow limited in some way other than the inherent meanings of the language and formulas literally used therein.

Aspect 1: A method comprising the steps of a) producing a hydrocarbon stream from syngas via a Fischer-Tropsch reaction, wherein the hydrocarbon stream comprises a first C2 hydrocarbon stream comprising ethane and a first ethylene product; b) separating at least a portion of the first C2 hydrocarbon stream from the hydrocarbon stream; c) separating at least a portion of the first ethylene product from the first C2 hydrocarbon stream, thereby producing a second C2 hydrocarbon stream; d) converting at least a portion of the ethane in the second C2 hydrocarbon stream to a second ethylene product; and e) producing polyethylene from at least a portion of the second ethylene product.

Aspect 2: The method of aspect 1, wherein the hydrocarbon stream comprises at least about 5 wt % of the first C2 hydrocarbon stream.

Aspect 3: The method of aspect 1, wherein the hydrocarbon stream comprises at least about 10 wt % of the first C2 hydrocarbon stream.

Aspect 4: The method of aspect 1, wherein the hydrocarbon stream comprises at least about 20 wt % of the first C2 hydrocarbon stream.

Aspect 5: The method of aspect 1, wherein the hydrocarbon stream comprises from about 10 wt % to about 30 wt % of the first C2 hydrocarbon stream.

Aspect 6: The method of any one of aspects 1-5, wherein the first C2 hydrocarbon stream comprises from about 30 wt % to about 70 wt % of ethane and from about 70 wt % to about 30 wt % of the first ethylene product.

Aspect 7: The method of any one of aspects 1-6, wherein the second C2 hydrocarbon stream comprises at least about 50 wt % of ethane.

Aspect 8: The method of any one of aspects 1-7, wherein the hydrocarbon stream further comprises from about 30 wt % to about 70 wt % of C3-C6 hydrocarbons.

Aspect 9: The method of any one of aspects 1-8, wherein the step of converting at least a portion the ethane in the second C2 hydrocarbon stream to a second ethylene product comprises dehydrogenating the at least a portion of the ethane in the second C2 hydrocarbon stream.

Aspect 10: The method of any one of aspects 1-8, wherein the step of converting at least a portion the ethane in the second C2 hydrocarbon stream to a second ethylene product comprises cracking the at least a portion of the ethane in the second C2 hydrocarbon stream.

Aspect 11: The method of any one of aspects 1-10, wherein the step of producing polyethylene from at least a portion of the second ethylene product comprises catalytically polymerizing the second ethylene product.

Aspect 12: The method of any one of aspects 1-11, wherein the polyethylene is low density polyethylene.

Aspect 13: The method of any one of aspects 1-11, wherein the polyethylene is high density polyethylene.

Aspect 14: The method of any one of aspects 1-11, wherein the polyethylene is ultra-high-molecular-weight-polyethylene.

Aspect 15: A method comprising the steps of: a) producing a hydrocarbon stream from syngas via a Fischer-Tropsch reaction, wherein the hydrocarbon stream comprises a first C2 hydrocarbon stream comprising ethane and a first ethylene product; b) separating at least a portion of the first C2 hydrocarbon stream from the hydrocarbon stream; c) separating at least a portion of the first ethylene product from the C2 hydrocarbon stream, thereby producing a second C2 hydrocarbon stream; d) converting at least a portion the ethane in the second C2 hydrocarbon stream to a second ethylene product; e) combining at least a portion of the first ethylene product and at least a portion of the second ethylene product, thereby producing a third ethylene product; and f) producing polyethylene from at least a portion of the third ethylene product.

Aspect 16: The method of aspect 15, wherein the hydrocarbon stream comprises at least about 5 wt % of the first C2 hydrocarbon stream.

Aspect 17: The method of aspect 15, wherein the hydrocarbon stream comprises at least about 10 wt % of the first C2 hydrocarbon stream.

Aspect 18: The method of aspect 15, wherein the hydrocarbon stream comprises at least about 20 wt % of the first C2 hydrocarbon stream.

Aspect 19: The method of aspect 15, wherein the hydrocarbon stream comprises from about 10 wt % to about 30 wt % of the C2 hydrocarbon stream.

Aspect 20: The method of any one of aspects 15-19, wherein the first C2 hydrocarbon stream comprises from about 30 wt % to about 70 wt % of ethane and from about 70 wt % to about 30 wt % of the first ethylene product.

Aspect 21: The method of any one of aspects 15-20, wherein the second C2 hydrocarbon stream comprises at least about 50 wt % of ethane.

Aspect 22: The method of any one of aspects 15-21, wherein the hydrocarbon stream further comprises from about 30 wt % to about 70 wt % of C3-C6 hydrocarbons.

Aspect 23: The method of any one of aspects 15-22, wherein the method further comprises the step of producing ethylene glycol from at least a portion of the ethylene oxide.

Aspect 24: The method of any one of aspects 15-23, wherein the step of converting at least a portion the ethane in the second C2 hydrocarbon stream to a second ethylene product comprises dehydrogenating the at least a portion of the ethane in the second C2 hydrocarbon stream.

Aspect 25: The method of any one of aspects 15-23, wherein the step of converting at least a portion the ethane in the second C2 hydrocarbon stream to a second ethylene product comprises cracking the at least a portion of the ethane in the second C2 hydrocarbon stream.

Aspect 26: The method of any one of aspects 15-23, wherein the step of producing polyethylene from at least a portion of the third ethylene product comprises catalytically polymerizing the second ethylene product.

Aspect 27: The method of any one of aspects 15-23, wherein the polyethylene is low density polyethylene.

Aspect 28: The method of any one of aspects 15-26, wherein the polyethylene is high density polyethylene.

Aspect 29: The method of any one of aspects 15-26, wherein the polyethylene is ultra-high-molecular-weight-polyethylene.

Aspect 30: A system comprising: a) a Fischer-Tropsch reactor comprising a first inlet and a first outlet; b) a deethanizer comprising a second inlet and a second outlet; c) an olefin separator comprising a third inlet and a third outlet; d) an ethane cracker comprising a fourth inlet and a fourth outlet or an ethane dehydrogenator comprising a fifth inlet and a fifth outlet; and e) a polyethylene reactor comprising a sixth inlet and a sixth outlet, wherein the Fischer-Tropsch reactor is in fluid communication with the deethanizer via a first connector, wherein the first connector is connected to the first outlet of the Fischer-Tropsch reactor and to the second inlet of the deethanizer, wherein the deethanizer is in fluid communication with the olefin separator via a second connector, wherein the second connector is connected to the second outlet of the deethanizer and to the third inlet of the olefin separator, wherein the olefin separator is in fluid communication with the ethane cracker or the ethane dehydrogenator via a third connector, wherein the third connector is connected to the third outlet of the olefin separator and to the fourth inlet of the ethane cracker or to the fifth inlet of the ethane dehydrogenator, wherein the ethane cracker or the ethane dehydrogenator is in fluid communication with the polyethylene reactor via a fourth connector, wherein the fourth connector is connected to the fourth outlet of the ethane cracker or to the fifth outlet of the ethane dehydrogenator and to the sixth inlet of the polyethylene reactor.

Aspect 31: The system of aspect 30, wherein the system comprises an ethane cracker.

Aspect 32: The system of aspect 30, wherein the system comprises an ethane dehydrogenator.

Aspect 33: The system of any one of aspects 30-32, wherein the system further comprises a syngas production reactor comprising an seventh outlet, wherein the syngas production reactor is in fluid communication with the Fischer-Tropsch reactor via fifth connector, wherein the Fischer-Tropsch reactor further comprises an eighth inlet, wherein the fifth connector is connected to the seventh outlet of the syngas production reactor and to the eighth inlet of the Fischer-Tropsch reactor.

Aspect 34: The system of any one of aspects 30-33, wherein the olefin separator is in fluid communication with the polyethylene reactor via a sixth connector.

Aspect 35: The system of any one of aspects 30-34, wherein the system is on an industrial scale.

What is claimed is:

1. A method comprising the steps of:
   a) producing a hydrocarbon stream from syngas via a Fischer-Tropsch reaction, wherein the hydrocarbon stream comprises a first C2 hydrocarbon stream comprising ethane and a first ethylene product;
   b) separating at least a portion of the first C2 hydrocarbon stream from the hydrocarbon stream in a deethanizer;
   c) separating at least a portion of the first ethylene product from the first C2 hydrocarbon stream, thereby producing a second C2 hydrocarbon stream;
   d) converting at least a portion of the ethane in the second C2 hydrocarbon stream to a second ethylene product; and
   e) producing polyethylene from at least a portion of the second ethylene product.

2. The method of claim 1, wherein the hydrocarbon stream comprises from about 10 wt % to about 30 wt % of the first C2 hydrocarbon stream.

3. The method of claim 1, wherein the first C2 hydrocarbon stream comprises from about 30 wt % to about 70 wt % of ethane and from about 70 wt % to about 30 wt % of the first ethylene product.

4. The method of claim 1, wherein the second C2 hydrocarbon stream comprises at least about 50 wt % of ethane.

5. The method of claim 1, wherein the hydrocarbon stream further comprises from about 30 wt % to about 70 wt % of C3-C6 hydrocarbons.

6. The method of claim 1, wherein the step of converting at least a portion the ethane in the second C2 hydrocarbon stream to a second ethylene product comprises dehydrogenating the at least a portion of the ethane in the second C2 hydrocarbon stream.

7. The method of claim 1, wherein the step of converting at least a portion the ethane in the second C2 hydrocarbon stream to a second ethylene product comprises cracking the at least a portion of the ethane in the second C2 hydrocarbon stream.

8. A method comprising the steps of:
   a) producing a hydrocarbon stream from syngas via a Fischer-Tropsch reaction, wherein the hydrocarbon stream comprises a first C2 hydrocarbon stream comprising ethane and a first ethylene product;

b) separating at least a portion of the first C2 hydrocarbon stream from the hydrocarbon stream in a deethanizer;
c) separating at least a portion of the first ethylene product from the C2 hydrocarbon stream, thereby producing a second C2 hydrocarbon stream;
d) converting at least a portion the ethane in the second C2 hydrocarbon stream to a second ethylene product;
e) combining at least a portion of the first ethylene product and at least a portion of the second ethylene product, thereby producing a third ethylene product; and
f) producing polyethylene from at least a portion of the third ethylene product.

9. The method of claim 8, wherein the hydrocarbon stream comprises from about 10 wt % to about 30 wt % of the C2 hydrocarbon stream.

10. The method of claim 8, wherein the first C2 hydrocarbon stream comprises from about 30 wt % to about 70 wt % of ethane and from about 70 wt % to about 30 wt % of the first ethylene product.

11. The method of claim 8, wherein the second C2 hydrocarbon stream comprises at least about 50 wt % of ethane.

12. The method of claim 8, wherein the hydrocarbon stream further comprises from about 30 wt % to about 70 wt % of C3-C6 hydrocarbons.

13. The method of claim 8, wherein the step of converting at least a portion the ethane in the second C2 hydrocarbon stream to a second ethylene product comprises dehydrogenating the at least a portion of the ethane in the second C2 hydrocarbon stream.

14. The method of claim 8, wherein the step of converting at least a portion the ethane in the second C2 hydrocarbon stream to a second ethylene product comprises cracking the at least a portion of the ethane in the second C2 hydrocarbon stream.

* * * * *